| United States Patent [19] | [11] Patent Number: 4,764,214 |
| Marx et al. | [45] Date of Patent: Aug. 16, 1988 |

[54] WOOD PRESERVATIVES CONTAINING 2-IODOBENZANILIDE

[75] Inventors: Hans-Norbert Marx, Buehl-Weitenung; Reimer Goettsche, Baden-Baden; Werner Klein, Birkenheide, all of Fed. Rep. of Germany

[73] Assignee: Wolman GmbH, Sinzheim, Fed. Rep. of Germany

[21] Appl. No.: 36,457

[22] Filed: Apr. 9, 1987

[30] Foreign Application Priority Data

Apr. 19, 1986 [DE] Fed. Rep. of Germany ....... 3613253

[51] Int. Cl.[4] .......................... C09D 5/16; B05D 1/18
[52] U.S. Cl. .................................. 106/18.32; 427/440
[58] Field of Search ..................... 106/18.32; 514/619, 514/617; 427/440

[56] References Cited

U.S. PATENT DOCUMENTS

| 3,431,265 | 3/1969 | Wakeman et al. | 106/18.32 |
| 3,435,039 | 3/1969 | Wakeman et al. | 106/18.32 |
| 3,969,510 | 7/1976 | Osieka et al. | 424/324 |
| 4,123,554 | 10/1978 | Kawada et al. | 514/617 |
| 4,585,795 | 4/1986 | Linderborg | 514/558 |

OTHER PUBLICATIONS

European standard draft prEN 113 published by European Committee for Standardization, p. 7.

*Primary Examiner*—Theodore Morris
*Attorney, Agent, or Firm*—Oblon, Fisher, Spivak, McClelland & Maier

[57] ABSTRACT

Wood preservatives contain a mixture of 2-iodobenzanilide with a quaternary ammonium compound.

20 Claims, No Drawings

WOOD PRESERVATIVES CONTAINING 2-IODOBENZANILIDE

BACKGROUND OF THE INVENTION

1. Field of the Invention

The present invention relates to wood preservatives which contain 2-iodobenzanilide and a quaternary ammonium compound.

2. Discussion of the Background

It has been disclosed that 2-iodobenzanilide has a good fungicidal action, for example against wood-destroying Basidiomycetes (DE-No. 16 42 224). However, it cannot be used in practice because of its poor solubility. The amount of active ingredient which has to be present in the wood preservatives to provide adequate protection of the wood from fungi (about 1–2% by weight for primers or transparent finishes) can, owing to its poor solubility in aliphatic and aromatic hydrocarbons, only be dissolved in the wood preservative by using a large amount (more than 10%) of special solvents (N-methylpyrrolidone/dimethylformamide). This has an adverse effect on the performance characteristics of the wood preservatives (drying).

It is also known that quaternary ammonium compounds can be used as cationic emulsifiers. They may be used in both aqueous and oily mixtures.

SUMMARY OF THE INVENTION

We have found that a mixture of 2-iodobenzanilide and a quaternary ammonium compound has very good fungicidal activity, in particular against Basidiomycetes fungi.

DETAILED DESCRIPTION OF THE PREFERRED EMBODIMENTS

The novel wood preservatives can be used in both oily and aqueous mixtures. It is also possible to treat woodworking materials with the wood preservatives.

By using special solvents, eg. tributyl phosphate, it is possible to prepare concentrates which can very easily be mixed with a mixture of other components of the wood preservatives. Because of the good fungicidal action of the novel wood preservative, a smaller amount of 2-iodobenzanilide, in the form of the novel wood preservative, is required to achieve a fungicidal effect identical to that obtained using 2-iodobenzanilide alone. Furthermore, this smaller amount of 2-iodobenzanilide requires a smaller amount of solvent to dissolve it. Another possible use of the novel wood preservatives is for protecting wood-base materials from fungal attack. The concentrates can either be mixed with the glue or sprayed onto the wood chips (for example during production of chipboard).

The mixtures according to the invention contain quaternary ammonium compounds and iodobenzanilide, for example in a weight ratio of from 1:2 to 20:1, preferably from 2:1 to 10:1.

Examples of suitable quaternary ammonium compounds are those of the general formula $(R^1R^2R^3R^4N)^+Z^-$, where $R^1$ is alkyl of 8 to 20, in particular 12 to 20 carbon atoms or is benzyl which is unsubstituted or substituted by $C_1$-$C_{20}$-alkyl or halogen, $R^2$ is $C_1$-$C_6$-alkyl or $C_3$-$C_9$-alkoxyalkyl, $R^3$ is $C_1$-$C_6$-alkyl or $C_1$-$C_4$-alkoxy and $R^4$ is $C_1$-$C_{20}$-alkyl, or two of the radicals $R^1$ to $R^4$, together with the nitrogen atom, form a heterocyclic radical which contains 4 or 5 carbon atoms, 1 or 2 nitrogen atoms and one, two or three double bonds, the carbon atoms being unsubstituted or substituted by $C_1$-$C_4$-alkyl or halogen, and Z is an acid radical.

The novel mixtures contain, for example, from 10 to 40, in particular from 15 to 35, % of 2-iodobenzanilide and from 90 to 60, in particular from 85 to 65, % of a quaternary ammonium compound. The ready-to-use wood preservative solutions or emulsions contain, for example, (a) in a mixture with hydrocarbons, 0.3–0.7% of 2-iodobenzanilide, 1.5–3.5% of a quaternary ammonium compound, 70–93% of liquid hydrocarbons, 5–6% of other organic solvents, 0–20% of an alkyd resin and 0–3% of pigments, the percentages summing to 100% in each case, and (b) in a concentrate for the emulsion with water, 3–7% of 2-iodobenzanilide, 30–50% of a quaternary ammonium compound, 10–20% of organic solvents (not hydrocarbons) and 30–50% of a nonionic emulsifier (based on ethylene oxide), the percentages summing to 100 in each case. 1 part of this concentrate is mixed with, for example, from 40 to 60 parts of water in order to obtain the ready-to-use aqueous agent.

In order to increase the action spectrum or to achieve special effects, the mixture containing the active ingredient may also be combined with other active ingredients. Particularly advantageous mixtures are those which contain, for example, the following compounds:

N-tridecyl-2,6-dimethylmorpholine organotin compounds, such as tributyltin oxide, tributyltin benzoate and tributyltin-N-cyclohexyl-N'-hydroxydiazenium oxide methylene bisthiocyanate dimethylalkylamine salts chlorophenols, such as tetra- and pentachlorophenol tetrachloroisophthalodinitrile N-cyclohexyl-N-methoxy-2,5-dimethylfuran-3-carboxamide N,N-dimethyl-N'-phenyl-(N-fluoromethylthio)-sulfamide N,N-dimethyl-N'-tolyl-(N-fluoromethylthio)-sulfamide methyl benzimidazole-2-carbamate 2-thiocyanomethylthiobenzothiazole copper naphthenate copper 8-hydroxyquinoline alkali metal and metal salts of N'-hydroxy-N-cyclohexyldiazenium oxide 1-(1',2',4'-triazol-1'-yl)-1-(4'-chlorophenoxy)-3,3-dimethylbutan-2-one 1-(1',2',4'-triazol-1'-yl)-1-(4'-chlorophenoxy)-3,3-dimethylbutan-2-ol N-(3-(p-tert-butylphenyl)-2-methylpropyl)-cis-2,6-dimethylmorpholine hexachlorocyclohexane O,O-diethyl 0-(α-cyanobenzylideneamino)thiophosphate O,O-diethyl 0-3,5,6-trichloropyrid-2-yl thionophosphate O,O-diethyldithiophosphorylmethyl-6-chlorobenzoxazolone 2-(1,3-thiazol-4-yl)-benzimidazole N-trichloromethylthio-3,6,7,8-tetrahydrophthalimide N-(1,1,2,2-tetrachloroethylthio)-3,6,7,8-tetrahydrophthalimide N-trichloromethylthiophthalimide 2-N-octyl-4-isothiazolin-3-one 1,2-benzisothiazole-3-one 1-(4-chlorophenoxy)-3,3-dimethyl-1-(1H-1,2,4-triazol-1-yl)butan-2-one
1-(4-chlorophenoxy)-3,3-dimethyl-1-(1H-1,2,3-triazol-2-yl)butan-2-ol
O,O-dimethyl S-(2-methylamino-2-oxoethyl)dithiophosphate
O,O-diethyl 0-(3,5,6-trichloropyrid-2-yl)thiophosphate
O,O-dimethyl S-(N-phthalimido)-methyl dithiophosphate
6,7,8,9,10-hexachloro-1,5,5a,6,9,9a-hexylhydro-6,9-methano-2,3,4-benzodioxothiepin-3-oxide
2-sec-butylphenyl N-methylcarbamate
2-isopropoxyphenyl N-methylcarbamate
naphth-1-yl N-methylcarbamate
norbornene dimethanolhexachlorocyclosulfite
1-(4-chlorophenyl)-3-(2,6-difluorobenzoyl)-urea synthetic pyrethroids, such as
3-phenoxybenzyl (±)-3-(2,2-dichlorovinyl)-2,2-dimethylcyclopropane-1-carboxylate,
alpha-cyano-3-phenoxybenzyl 3-(2,2-dichlorovinyl)-2,2-dimethylcyclopropane-1-carboxylate,
alpha-cyano-m-phenoxybenzyl 3-(2,2-dibromovinyl)-2,2-dimethyl(1R,3R)cyclopropanecarboxylate and
alpha-cyano-3-phenoxybenzyl alpha-isopropyl-4-chlorophenylacetate.

The Examples which follow illustrate the invention. The threshold values for Basidiomycetes after impregnated pieces of wood had been washed out were determined for pine sapwood using water or acetone as the solvent.

Unless stated otherwise, the dimethylalkylbenzylammonium chloride used in the following comparative agents and novel mixtures contains an alkyl radical in which the chain length is predominantly more than 10 carbon atoms, eg. 40% of $C_{12}$, 50% of $C_{14}$ and 10% of $C_{16}$.

EXAMPLE 1 (Comparison)

Solvent: water
Dimethylalkylbenzylammonium chloride (100%)

| Test fungus: | Threshold value kg/m$^3$ |
|---|---|
| *Poria vaporaria* | 1.8–2.8 kg/m$^3$ |
| *Coniophora puteana* | 2.8–4.4 kg/m$^3$ |

EXAMPLE 2 (Comparison)

Solvent: water
Dimethyldialkylammonium chloride
(Alkyl: more than 90% of $C_{10}$)

| Test fungus: | Threshold value kg/m$^3$ |
|---|---|
| *Poria vaporaria* | 1.1–1.8 kg/m$^3$ |
| *Coniophora puteana* | 1.8–2.8 kg/m$^3$ |

EXAMPLE 3 (Comparison)

Solvent: water
Trimethylcetylammonium bromide

| Test fungus: | Threshold value kg/m$^3$ |
|---|---|
| *Poria vaporaria* | 1.2–2.8 kg/m$^3$ |
| *Coniophora puteana* | 2.8–4.4 kg/m$^3$ |

EXAMPLE 4 (Comparison)

Solvent: acetone
2-Iodobenzanilide

| Test fungus: | Threshold value kg/m$^3$ |
|---|---|
| *Poria vaporaria* | 2.4–5.0 kg/m$^3$ |
| *Coniophora puteana* | 0.5–1.2 kg/m$^3$ |

EXAMPLE 5

(According to the invention)

Solvent: acetone
20% of iodobenzanilide
80% of dimethylalkylbenzylammonium chloride

| Test fungus: | Threshold value kg/m$^3$ |
|---|---|
| *Poria vaporaria* | 0.5–0.9 kg/m$^3$ |
| *Coniophora puteana* | 0.9–1.2 kg/m$^3$ |

EXAMPLE 6

(According to the invention)

Solvent: acetone
33% of iodobenzanilide
67% of dimethyldialkylammonium chloride
(alkyl: more than 90% of $C_{10}$)

| Test fungus: | Threshold value kg/m$^3$ |
|---|---|
| *Poria vaporaria* | 0.5–0.9 kg/m$^3$ |
| *Coniophora puteana* | 0.3–0.5 kg/m$^3$ |

EXAMPLE 7

(According to the invention)

Solvent: acetone
15% of iodobenzanilide
85% of trimethylcetylammonium chloride

| Test fungus: | Threshold value kg/m$^3$ |
|---|---|
| *Poria vaporaria* | 0.5–0.9 kg/m$^3$ |
| *Coniophora puteana* | 0.9–1.2 kg/m$^3$ |

USE EXAMPLE 1

Wood preservative oil
0.50% of iodobenzanilide
3.00% of dimethylalkylbenzylammonium chloride
1.00% of ethanol
5.00% of tributyl phosphate
91.50% of a 5:1 aliphatic/aromatic gasoline mixture, boiling range about 180°–220° C.

USE EXAMPLE 2

Wood preservative primer
0.50% of iodobenzanilide
2.70% of dimethylalkylbenzylammonium chloride
0.90% of ethanol
5.00% of tributyl phosphate
6.00% of a long-oil linseed oil alkyd resin
84.90% of a 5:1 aliphatic/aromatic gasoline mixture, boiling range about 180°–220° C.

USE EXAMPLE 3

Transparent wood finish
0.50% of iodobenzanilide
2.00% of dimethylalkylbenzylammonium chloride
0.40% of ethanol
5.00% of tributyl phosphate
15.00% of a long-oil alkyd resin (based on soybean oil/linseed oil)
0–3% of pigment formulations (iron oxide, carbon black)
77.1–73.1% of a 5:1 aliphatic/aromatic gasoline mixture, boiling range about 180°–220° C.

USE EXMPLE 4

Aqueous wood preservative
5.00% of iodobenzanilide
5.00% of tributyl phosphate
40.00% of dimethylalkylbenzylammonium chloride
10.00% of ethanol
40.00% of oxyethylated nonylphenol (about 10 moles of ethylene oxide per mole of nonylphenol)
2 parts of this mixture emulsified in 98 parts of water give a clear emulsion, for example for pressure processes.

USE EXAMPLE 5

Concentrate for preserving woodworking materials
25.00% of iodobenzanilide
25.00% of tributyl phosphate
40.00% of dimethylalkylbenzylammonium chloride
10.00% of ethanol
0.75 Part of this mixture (mixed with glue) is sprayed onto 100 parts of dry wood chips.

We claim:

1. A wood preservative composition comprising 2-iodobenzanilide and a quaternary ammonium compound, wherein:
   (1) said 2-iodobenzanilide and said quaternary ammonium compounds are present in a weight ratio of from 2:1 to 1:20; and
   (2) said quaternary ammonium compound is a compound of the formula $(R^1R^2R^3R^4N)^+X^-$, wherein $R_1$ is a $C_{8-20}$ alkyl, benzyl, or benzyl substituted by $C_{1-20}$ alkyl or halogen, $R_2$ is $C_1$–$C_6$-alkyl or $C_3$–$C_9$-alkoxyalkyl, $R^3$ is $C_1$–$C_6$-alkyl or $C_{1-4}$ alkoxy, $R^4$ is $C_{1-20}$ alkyl, or wherein any two of radicals $R^1$ to $R^4$, together with the nitrogen atom, form a heterocyclic radical containing 4 or 5 carbon atoms, 1 or 2 nitrogen atoms, and 1, 2 or 3 double bonds, or wherein any two of radicals $R_1$ to $R_4$, together with the nitrogen atom, form a heterocyclic radical containing 4 or 5 carbon atoms, 1 or 2 nitrogen atoms, and 1, 2 or 3 double bonds, said carbon atoms being substituted by $C_{1-4}$ alkyl or halogen, and Z is an acid radical.

2. The composition of claim 1, further comprising a solvent.

3. The composition of claim 2, wherein said solvent is water.

4. The composition of claim 2, wherein said solvent is a mixture of liquid hydrocarbon.

5. The composition of claim 1, further comprising tributylphosphate.

6. The composition of claim 1, comprising said 2-iodobenzanilide and said quaternary ammonium compound in a weight ratio of from 1:2 to 1:10.

7. The composition of claim 1, wherein $R_1$ is $C_{12-20}$ alkyl.

8. The composition of claim 1, comprising from 10 to 40% of 2-iodobenzanilide and from 90 to 60% of said quaternary ammonium compound.

9. The composition of claim 1, comprising from 15 to 35% of said 2-iodobenzanilide and from 85 to 65% of said quaternary ammonium compound.

10. The composition of claim 1, comprising:
   (a) in a mixture with hydrocarbons, 0.3 to 0.7% of 2-iodobenzanilide, 1.5 to 3.5% of a quaternary ammonium compound, 70 to 93% of a liquid hydrocarbon, 5 to 6% of another organic solvent, 0 to 20% of an alkyd resin and 0 to 3% of a pigment, wherein the percentages add up to 100% in each case, or
   (b) in a concentrate for emulsion with water, 3 to 7% of 2-iodobenzanilide, 30 to 50% of a quaternary ammonium compound, 10 to 20% of an organic solvent other than a hydrocarbon, and 30 to 50% of a nonionic emulsifier based on ethylene oxide, wherein the percentages add up to 100 in each case.

11. The composition of claim 10, comprising in a mixture with hydrocarbons, 0.3 to 0.7% of 2-iodobenzanilide, 1.5 to 3.5% of a quaternary ammonium compound, 70 to 93% of a liquid hydrocarbon, 5 to 6% of another organic solvent, 0 to 20% of an alkyd resin, and 0 to 3% of a pigment wherein the percentages add up to 100% in each case.

12. The composition of claim 10, comprising, in a concentrate for emulsion with water, 3 to 7% of 2-iodobenzanilide, 30 to 50% of a quaternary ammonium compound, 10 to 20% of an organic solvent other than a hydrocarbon, and 30 to 50% of a nonionic emulsifier based on ethylene oxide, the percentages summing to 100% in each case.

13. The composition of claim 1, comprising an additional active ingredient which is at least one member selected from the group consisting of N-tridecyl-2,6-dimethylmorpholine; organotin compounds; methylene bisthiocyanate; dimethylalkylamine salts; chlorophenols; tetrachloroisophthalodinitrile; N-cyclohexyl-N-methoxy-2,5-dimethylfuran-3-carboxamide; N,N-dimethyl-N'-phenyl-(N-fluoromethylthio)-sulfamide; N,N-dimethyl-N'-tolyl-(N-fluoromethylthio)-sulfamide; methyl benzimidazole-2-carbamate; 2-thiocyanomethylthiobenzothiazole; copper naphthenate; copper 8-hydroxyquinoline; alkali metal and metal salts of N'-hydroxy-N-cyclohexyl-diazenium oxide; 1-(1',2',4'-triazol-1'-yl)-1-(4'-chlorophenoxy)-3,3-dimethylbutan-2-one; 1-(1',2',4'-triazol-1'-yl)-1-(4'-chlorophenoxy)-3,3-dimethylbutan-2-ol; N-(3-p-tert-butylphenyl)-2-methylpropyl)-cis-2,6-dimethylmorpholine; hexachlorocyclohexane; O,O-diethyl 0-(α-cyanobenzylideneamino)thiophosphate; O,O-diethyl 0-3,5,6-trichloropyrid-2-yl thionophosphate; O,O-diethyldithiophosphorylmethyl-6-chlorobenzoxazolone; 2-(1,3-thiazol-4-yl)-benzimidazole; N-trichloromethylthio-3,6,7,8-tetrahydrophthalimide; N-(1,1,2,2-tetrachloroethylthio)-3,6,7,8-tetrahydrophthalimide; N-trichloromethylthiophthalimide; 2-N-octyl-4-isothiazolin-3-one; 1,2-benzisothiazole-3-one; 1-(4-chlorophenoxy)-3,3-dimethyl-1-(1H-1,2,4-triazol-1-yl)butan-2-one; 1-(4-chlorophenoxy)-3,3-dimethyl-1-(1H-1,2,3-triazol-2-yl)butan-2-ol; O,O-dimethyl S-(2-methylamino-2-oxoethyl)dithiophosphate; O,O-diethyl 0-(3,5,6-trichloropyrid-2-yl)thiophosphate; O,O-dimethyl S-(N-phthalimido)-methyl dithiophosphate; 6,7,8,9,10-hexachloro-1,5,5a,6,9,9a-hexylhydro-6,9-methano-2,3,4-benzodioxothiepin-3-oxide; 2-sec-butylphenyl N-methylcarbamate; 2-isopropoxyphenyl N-methylcarbamate; naphth-1-yl N-methylcarbamate; norbornene dimethanolhexachlorocyclosulfite; 1-(4-chlorophenyl)-3-(2,6-difluorobenzoyl)-urea; and synthetic pyrethroids.

14. The composition of claim 13, wherein said organotin compound comprises tributyltin oxide, tributyltin benzoate and tributyltin-N-cyclohexyl-N'-hydroxydiazenium oxide, or wherein said synthetic pyrethroids comprise 3-phenoxybenzyl(±)-3-(2,2-dichlorovinyl)-2,2-dimethylcyclopropane-1-carboxylate, α-cyano-3-phenoxybenzoyl-3-(2,2-dichlorovinyl)-2,2-dimethylcyclopropane-1-carboxylate, α-cyano-m-phenoxybenzyl-3-(2,2-dibromovinyl)-2,2-dimethyl(1R,2R)cyclopropane carboxylate or α-cyano-3-phenoxybenzyl α-isopropyl-4-chlorophenylacetate.

15. A method for preserving wood, comprising treating wood with a composition comprising 2-iodobenzanilide and a quaternary ammonium compound, wherein:
   (1) said composition comprises said 2-iodobenzanilide and said quaternary ammonium compound in a weight ratio of from 2:1 to 1:20; and
   (2) said quaternary ammonium compound is a compound of the general formula $(R^1R^2R^3R^4N)^+Z^-$, wherein $R^1$ is a $C_{8-20}$ alkyl, benzyl or benzyl substituted by $C_{1-20}$ alkyl or halogen, $R^2$ is $C_{1-6}$ alkyl or $C_{3-9}$ alkyoxylkyl, $R^3$ is $C_{1-6}$ alkyl or $C_{1-4}$ alkoxy, $R^4$ is $C_{1-20}$ alkyl, or wherein any two of radicals $R^1$ to $R^4$, together with the nitrogen atom, form a heterocyclic radical containing 4 or 5 carbon atoms, 1 or 2 nitrogen atoms and 1, 2 or 3 double bonds, or wherein any two of radicals $R^1$ to $R^4$ together with the nitrogen atom form a heterocyclic radical containing 4 or 5 carbon atoms, 1 or 2 nitrogen atoms and 1, 2 or 3 double bonds, wherein said carbon atoms are substituted by $C_{1-4}$ alkyl or halogen, and Z is an acid radical.

16. The method of claim 15, comprising treating a wood with a composition comprising 2-iodobenzanilide, a quaternary ammonium compound and a solvent.

17. The method of claim 16, wherein said solvent is water or a mixture of liquid hydrocarbons.

18. The method of claim 15, wherein said composition comprises said 2-iodobenzanilide and said quaternary ammonium compound in a weight ratio of from 1:2 to 1:10.

19. The method of claim 15, wherein $R^1$ is $C_{12-20}$ alkyl.

20. The method of claim 15, wherein said composition comprises:
   (a) in a mixture with hydrocarbons, 0.3 to 0.7% of 2-iodobenzanilide, 1.5 to 3.5% of a quaternary ammonium compound, 70 to 93% of a liquid hydrocarbon, 5 to 6% of another organic solvent, 0 to 20% of an alkyd resin and 0 to 3% of a pigment, wherein the percentages add up to 100% in each case, or
   (b) in a concentrate for emulsion with water, 3 to 7% of 2-iodobenzanilide, 30 to 50% of a quaternary ammonium compound, 10 to 20% of an organic solvent other than a hydrocarbon, and 30 to 50% of a nonionic emulsifier based on ethylene oxide, wherein the percentages add up to 100 in each case.

* * * * *